(12) United States Patent
Mace et al.

(10) Patent No.: US 9,101,302 B2
(45) Date of Patent: Aug. 11, 2015

(54) ANALYTE TEST DEVICE

(75) Inventors: Chad Harold Mace, Hudson, NH (US); Paul Sen Yang, Witney (GB); Farzad Shahrokni, Swindon (GB)

(73) Assignee: Abbott Diabetes Care Inc., Alameda, CA (US)

( * ) Notice: Subject to any disclaimer, the term of this patent is extended or adjusted under 35 U.S.C. 154(b) by 865 days.

(21) Appl. No.: 10/837,886

(22) Filed: May 3, 2004

(65) Prior Publication Data

US 2005/0245844 A1 Nov. 3, 2005

(51) Int. Cl.
*A61B 5/145* (2006.01)
*A61B 5/15* (2006.01)
*A61B 5/1486* (2006.01)

(52) U.S. Cl.
CPC ........... *A61B 5/14532* (2013.01); *A61B 5/1411* (2013.01); *A61B 5/1486* (2013.01); *A61B 2562/0295* (2013.01)

(58) Field of Classification Search
CPC .......................... A16B 5/1411; A16B 5/1486
USPC .......................................... 600/345, 347, 365
See application file for complete search history.

(56) References Cited

U.S. PATENT DOCUMENTS 4,580,564 A  4/1986 Andersen
4,653,513 A * 3/1987 Dombrowski ................ 600/578

(Continued)

FOREIGN PATENT DOCUMENTS

EP  1 389 443 A1  2/2004
EP  1 426 758 A1  6/2004

(Continued)

OTHER PUBLICATIONS steep1. (2007). In the Ameircan Heritage® Dictionary of the English Language. Retrieved Jul. 24, 2008, from http://www.credoreference.com/entry/7130516.*

(Continued)

*Primary Examiner* — Patricia Mallari
*Assistant Examiner* — Michael Catina
(74) *Attorney, Agent, or Firm* — Edward J. Baba; Brian E. Davy; Bozicevic, Field & Francis LLP

(57) ABSTRACT

An analyte test device is constructed as an integrated, single-use, disposable cartridge which can be releasably installed into a compatible analyte test monitor. In use, the device can be used in conjunction with the monitor to lance the skin of a patient to create a blood sample, express the blood sample from the wound site using vacuum forces and calculate the concentration of a particular analyte in the expressed blood sample. In one embodiment, the device includes a base which includes a top surface and a bottom surface. The base is also shaped to define an aperture which extends transversely through its top and bottom surfaces. An electrochemical test sensor is affixed to the base in such a manner so that a vacuum path is at least partially defined between the base and the test sensor, the vacuum path being in fluid communication with the aperture. A cover is affixed to the top surface of the base over the aperture, the cover comprising a flexible dome-shaped member and a lancet coupled to the member, the lancet being orientated such that its longitudinal axis extends at an approximate right angle relative to the longitudinal axis of the test sensor. The bottom surface of the base is shaped to include a skin receiving surface which at least partially defines the aperture in the base, the skin receiving surface having a steep inward contour to distend the skin of the patient when pressed thereagainst.

47 Claims, 10 Drawing Sheets

(56) References Cited

U.S. PATENT DOCUMENTS

| | | | |
|---|---|---|---|
| 5,054,499 A * | 10/1991 | Swierczek | 600/583 |
| 5,080,865 A * | 1/1992 | Leiner et al. | 422/68.1 |
| 5,152,775 A | 10/1992 | Ruppert | |
| 5,201,324 A * | 4/1993 | Swierczek | 600/583 |
| 5,231,993 A * | 8/1993 | Haber et al. | 600/583 |
| 5,390,671 A * | 2/1995 | Lord et al. | 600/347 |
| 5,636,640 A * | 6/1997 | Staehlin | 600/577 |
| 5,714,390 A * | 2/1998 | Hallowitz et al. | 436/526 |
| RE35,803 E | 5/1998 | Lange et al. | |
| 5,872,713 A | 2/1999 | Douglas et al. | |
| 5,942,102 A | 8/1999 | Hodges et al. | |
| 5,997,817 A | 12/1999 | Crismore et al. | |
| 6,027,459 A | 2/2000 | Shain et al. | |
| 6,063,039 A | 5/2000 | Cunningham et al. | |
| 6,071,294 A | 6/2000 | Simons et al. | |
| 6,093,156 A | 7/2000 | Cunningham et al. | |
| 6,143,164 A * | 11/2000 | Heller et al. | 600/583 |
| 6,174,420 B1 | 1/2001 | Hodges et al. | |
| 6,179,999 B1 | 1/2001 | Sherman et al. | |
| 6,299,757 B1 * | 10/2001 | Feldman et al. | 205/775 |
| 6,306,104 B1 | 10/2001 | Cunningham et al. | |
| 6,352,514 B1 | 3/2002 | Douglas et al. | |
| 6,377,894 B1 | 4/2002 | Deweese et al. | |
| 6,416,641 B1 * | 7/2002 | Ikeda et al. | 204/403.04 |
| 6,464,649 B1 | 10/2002 | Duchon et al. | |
| 6,506,168 B1 | 1/2003 | Fathallah et al. | |
| 6,540,891 B1 | 4/2003 | Stewart et al. | |
| 6,544,475 B1 | 4/2003 | Douglas et al. | |
| 6,561,989 B2 | 5/2003 | Whitson | |
| 6,602,268 B2 | 8/2003 | Kuhr et al. | |
| 6,616,616 B2 | 9/2003 | Fritz et al. | |
| 6,679,841 B2 * | 1/2004 | Bojan et al. | 600/309 |
| 6,706,049 B2 | 3/2004 | Moerman | |
| 6,767,440 B1 | 7/2004 | Bhullar et al. | |
| 6,849,052 B2 | 2/2005 | Uchigaki et al. | |
| 6,949,111 B2 | 9/2005 | Schraga | |
| 7,037,277 B1 * | 5/2006 | Smith et al. | 600/584 |
| 7,041,057 B1 * | 5/2006 | Faupel et al. | 600/365 |
| 7,133,712 B2 * | 11/2006 | Cohan et al. | 600/345 |
| 7,211,096 B2 | 5/2007 | Kuhr et al | |
| 7,238,192 B2 | 7/2007 | List et al. | |
| 7,273,484 B2 | 9/2007 | Thoes et al. | |
| 7,303,726 B2 | 12/2007 | McAllister et al. | |
| 7,316,700 B2 | 1/2008 | Alden et al. | |
| 2002/0016606 A1 * | 2/2002 | Moerman | 606/181 |
| 2002/0099308 A1 | 7/2002 | Bojan et al. | |
| 2003/0050573 A1 | 3/2003 | Kuhr et al. | |
| 2003/0212345 A1 | 11/2003 | McAllister et al. | |
| 2003/0233112 A1 | 12/2003 | Alden et al. | |
| 2004/0049129 A1 | 3/2004 | Qi | |
| 2004/0127818 A1 * | 7/2004 | Roe et al. | 600/583 |
| 2004/0162573 A1 | 8/2004 | Kheiri | |
| 2006/0287664 A1 | 12/2006 | Grage, Jr. et al. | |
| 2007/0156163 A1 | 7/2007 | Davison et al. | |
| 2008/0058848 A1 | 3/2008 | Griffin et al. | |

FOREIGN PATENT DOCUMENTS

| | | | |
|---|---|---|---|
| WO | WO 01/54570 A1 * | 8/2001 | A61B 5/00 |
| WO | 03/025559 A1 | 3/2003 | |
| WO | 03/087775 A2 | 10/2003 | |
| WO | WO 2005/107594 A1 | 11/2005 | |
| WO | WO 2005/107594 A2 | 3/2006 | |

OTHER PUBLICATIONS

PCT Search Report.

* cited by examiner

ANALYTE TEST DEVICE

BACKGROUND OF THE INVENTION

The present invention relates generally to integrated lancing and analytical devices and more particularly to a novel integrated lancing and analytical device.

There are many medical conditions which require frequent measurement of the concentration of a particular analyte in the blood of a patient. For example, diabetes is a disease which typically requires a patient to routinely measure the concentration of glucose in his/her blood. Based upon the results of each blood glucose measurement, the patient may then require a particular drug treatment (e.g., an injection of insulin) in order to regulate that the blood glucose level of the patient remains within a specified range. Exceeding the upper limit of said range (hyperglycemia) or dropping beneath the lower limit of said range (hypoglycemia) should be avoided with as much diligence as possible to prevent the patient from experiencing serious medical complications which include, inter alia, retinopathy, nephropathy, and neuropathy.

A multi-step process is commonly practiced by diabetes patients to self-monitor the level of glucose present in their blood.

In the first step of said process, a patient is required to provide a blood sample suitable for testing. Blood samples taken from a patient for blood sugar monitoring are typically obtained by piercing the skin of the patient using a lancet device. A lancet device typically includes a body and a lancet. The body is typically adapted to be held by the user, the lancet being coupled to the body and being adapted to penetrate through the epidermis (the outermost layer of the skin) of the patient and into the dermis (the layer of skin directly beneath the epidermis) which is replete with capillary beds. The puncture of one or more capillaries by the lancet generates a sample of blood which exits through the incision in the patient's skin.

In some lancet devices, the lancet extends from the body at all times. In other lancet devices, the lancet is adapted to be moved, when actuated, from a retracted position in which the lancet tip is disposed within the body to an extended position in which the lancet tip extends beyond the body. Typically, the movement of the lancet from its retracted position to its extended position is effected with such force that contact of the moving lancet tip with the skin of a patient results in the piercing of the skin of the patient. In many such lancet devices having a movable lancet, the lancet is automatically drawn back into the body after reaching its extended position in order to minimize the risk of inadvertent lancet sticks.

In the second step of said process, a blood glucose monitoring system is utilized to measure the concentration of glucose in the blood sample. One type of glucose monitoring system which is well known and widely used in the art includes a blood glucose meter (also commonly referred to a blood glucose monitor) and a plurality of individual, disposable, electrochemical test strips which can be removably loaded into the meter. Examples of blood glucose monitoring systems of the type described above are manufactured and sold by Abbott Laboratories, Medisense Products of Bedford, Mass. under the PRECISION line of blood glucose monitoring systems.

Each individual electrochemical test strip typically includes a substrate which is formed as a thin, rectangular strip of non-conductive material, such as plastic. A plurality of carbon-layer electrodes are deposited on the substrate along a portion of its length in a spaced apart relationship, one electrode serving as the reference electrode for the test strip and another electrode serving as the working electrode for the test strip. All of the conductive electrodes terminate at one end to form a reaction area for the test strip. In the reaction area, an enzyme is deposited on the working electrode. When exposed to the enzyme, glucose present in a blood sample undergoes a chemical reaction which produces a measurable electrical response. The other ends of the electrical contacts are disposed to electrically contact associated conductors located in the blood glucose monitor, as will be described further below.

A blood glucose monitor is typically modular and portable in construction to facilitate its frequent handling by the patient. A blood glucose monitor often comprises a multi-function test port which is adapted to receive the test strip in such a manner so that an electrical communication path is established therebetween. As such, an electrical reaction created by depositing a blood sample onto the reaction area of the test strip travels along the working electrode of the test strip and into the test port of the blood glucose monitor. Within the housing of the monitor, the test port is electrically connected to a microprocessor which controls the basic operations of the monitor. The microprocessor, in turn, is electrically connected to a memory device which is capable of storing a multiplicity of blood glucose test results.

In use, the blood glucose monitoring system of the type described above can be used in the following manner to measure the glucose level of a blood sample and, in turn, store the result of said measurement into memory as test data. Specifically, a disposable test strip is unwrapped from its packaging and is inserted into the test port of the monitor. With the test strip properly inserted into the monitor, there is established a direct electrical contact between the conductors on the test strip and the conductors contained within the test port, thereby establishing an electrical communication path between the test strip and the monitor. Having properly disposed the test strip into the test port, the monitor typically displays a "ready" indication on its display.

The user is then required to provide a blood sample using a lancing device. Specifically, a disposable lancet is unwrapped from its protective packaging and is loaded into a corresponding lancing device. The lancing device is then loaded, if necessary, and fired into the skin of the patient to provide a blood sample.

After lancing the skin, the patient is required to deposit one or more drops of blood from the patient's wound site onto the reaction area of the test strip. When a sufficient quantity of blood is deposited on the reaction area of the test strip, an electrochemical reaction occurs between the blood sample and the enzyme deposited on the working electrode which, in turn, produces an electrical current which decays exponentially over time. The decaying electrical current created through the chemical reaction between the enzyme and the glucose molecules in the blood sample, in turn, travels along the electrically conductive path established between the test strip and the monitor and is measured by the microprocessor of the monitor. The microprocessor of the monitor, in turn, correlates the declining current to a standard numerical glucose value (e.g., using a scaling factor). The numerical glucose value calculated by the monitor is then shown on the monitor display for the patient to observe. In addition, the data associated with the particular blood glucose measurement is stored into the memory for the monitor.

A principal drawback associated with diabetes management systems of the type described above is that the lancing and glucose measurement operations are performed independently of one another. As a result, the user is required to possess both a lancet device and a blood glucose test monitor (as well as an individually packaged lancet and test strip) in order to perform a single assay. Furthermore, because the lancing and glucose measurement operations are performed independently of one another, the aforementioned process for performing an assay is relatively complicated and requires a considerably high level of manual dexterity, which is highly undesirable.

Accordingly, some diabetes management systems presently available in the market include a single blood glucose test monitor which is capable of performing both the lancing and glucose measurement operations. One type of glucose monitoring system which includes a single meter for performing both the lancing and glucose measurement operations is manufactured and sold by Abbott Laboratories, Medisense Products of Bedford, Mass. under the SOF•TACR™ line of diabetes management systems. The SOF•TACT™ blood glucose meter is represented, inter alia, in U.S. Pat. No. 6,506,168, which is incorporated herein by reference.

The SOF•TACT™ blood glucose meter is adapted to receive both a single disposable lancet and a single disposable test strip. In order to prepare the meter for an assay, the patient is required to open a pivotally mounted cover. With the cover opened, the patient is required to unwrap an individually sealed lancet and, in turn, mount the unwrapped lancet in a cylindrical lancet holder. In addition, the patient is required to unwrap an individually sealed test strip and, in turn, insert the unwrapped test strip into a test strip port. With a lancet and a test strip installed into the meter as described above, the cover is pivoted closed. To commence an assay, the patient positions a specified region of the monitor against his/her skin and presses an activation button. Depression of the activation button creates a pressure gradient which drives the lancet through an opening in the pivotable cover and into the patient's skin. The pressure gradient is then removed which retracts the lancet to its original unfired position.

After an opening has been formed in the skin of the patient, the blood sample is collected so that an assay can be performed. Specifically, a vacuum pump is used to draw blood from the wound site and in the direction towards the test strip. Simultaneously, mechanical linkages within the monitor use pressure to move the test strip towards the opening in the pivotable cover such that blood emerging from the patient's skin collects onto the reaction area of the test strip. When a sufficient amount of blood has been collected, the vacuum pump is deactivated. The meter then performs the assay based upon the electrochemical signal generated by the test strip and displays the result on an LCD screen.

Upon completion of the assay, the user is required to pivot open the cover of the meter and remove the used test strip and lancet. Because each test strip and lancet is designed for a single-use, the used test strip and lancet are discarded. The cover is then closed until future tests are required, at which time, the above-described process is repeated.

Although the SOF•TACT™ meter effectively combines both lancing and measurement processes into a single system, the user is still required to store and use two separate disposable products (i.e., a lancet and a test strip) in order to perform a single assay. As can be appreciated, the requirement that the user store, unwrap, load and discard two separate disposable items renders the system still somewhat complex to use.

Accordingly, some diabetes management systems which are known in the art require only the following two items in order to complete a blood glucose test: (1) a single blood glucose test monitor capable of performing both the lancing and glucose measurement operations and (2) an integrated, disposable, single-use test cartridge which includes both the lancing and analytical components (said cartridge being commonly referred to in the art as an integrated lancing and analytical device or simply as an integrated disposable).

As an example of an integrated lancing and analytical device, in U.S. Pat. No. 6,071,294 there is disclosed a cartridge for sampling and analyzing blood from the skin of a patient. The cartridge has a cartridge case, a lancet, and associated with the cartridge case an analytical region for analyzing the property of blood. The lancet has a tip for lancing the skin and is housed in the cartridge case. The lancet is operatively connected to the cartridge case such that the lancet can be pushed to extend its tip outside the cartridge case for lancing the skin to yield blood. The blood from the lancing wound is transferred to the analytical region and is analyzed.

As can be appreciated, the principal benefit of a system which uses integrated lancing and analytical devices is the simplicity in which a patient can perform an assay. Specifically, a patient is required only to unwrap and load a single cartridge into a corresponding meter prior to performing the assay. When an assay is required, the user is only required to place his/her finger against a region of the cartridge and, subsequent thereto, depress a suitable trigger or button. As a result, the number and relatively complexity of steps which the patient is required to perform is significantly reduced, which is highly desirable.

However, it should be noted that conventional integrated lancing and analytical devices suffer from a notable drawback. Specifically, blood glucose monitoring systems which use integrated disposable cartridges of the type described above typically include no means for drawing the blood sample from the wound site after lancing and, in turn, directing the drawn blood sample to the reaction area of the test strip. Rather, these systems typically require the user to manually expresses blood from his/her finger (e.g., by squeezing or massaging the skin surrounding the wound site). The user then orientates his/her finger such that the expressed blood droplets collect on the reaction area of the test strip. It should be noted that, because these systems include no means for expressing blood from the wound site and, in turn, directing the expressed blood to the reaction area of the test strip, a larger blood sample is often required from the patient, thereby increasing the overall level of discomfort experienced by the patient.

SUMMARY OF THE INVENTION

It is an object of the present invention to provide a novel analyte test device.

It is another object of the present invention to provide a novel analyte test device which can be removably installed into a compatible analyte test monitor.

It is yet another object of the present invention to provide a novel analyte test device of the type described above which, in conjunction with said compatible analyte test monitor, can be used to draw a blood sample and, in turn, measure the concentration of a particular analyte in said blood sample.

It is still another object of the present invention to provide an analyte test device of the type described above which, in conjunction with said compatible analyte test monitor, draws an adequate blood sample with minimal discomfort to the patient.

It is yet still another object of the present invention to provide an analyte test strip of the type described above which, in conjunction with said compatible analyte test monitor, is easy to use.

Therefore, according to one feature of the present invention, there is provided an analyte test device which is adapted to be removably coupled to a compatible analyte test meter, said analyte test device comprising a base, said base including a top surface, a bottom surface, a first end and a second end, said base being shaped to define an aperture which extends transversely through its top and bottom surfaces, an analyte test sensor coupled to said base, said base and said test sensor together at least partially defining a vacuum path in fluid communication with said aperture, and a cover coupled to the top surface of said base over the aperture.

According to another feature of the present invention, there is provided an analyte test device which is adapted to be removably coupled to a compatible analyte test meter, said analyte test device comprising an analyte test sensor, said analyte test sensor comprising a substrate and a reaction area on said substrate, said substrate comprising a top surface, a bottom surface, a first end and a second end, said substrate being shaped to define an aperture which extends transversely through its top and bottom surfaces, and a flexible member coupled to the top surface of the substrate over the aperture, said flexible member comprising a lancet adapted to selectively penetrate through the aperture in the substrate.

Various other features and advantages will appear from the description to follow. In the description, reference is made to the accompanying drawings which form a part thereof, and in which is shown by way of illustration, various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF THE PREFERRED EMBODIMENT

Figure 1A:
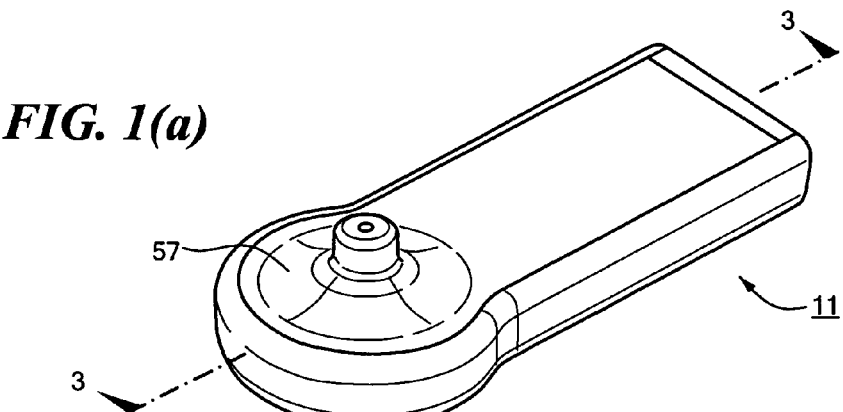
FIG. 1(a) is a top, front perspective view of a first embodiment of an analyte test device which is constructed according to the teachings of the present invention.
Figure 1B:
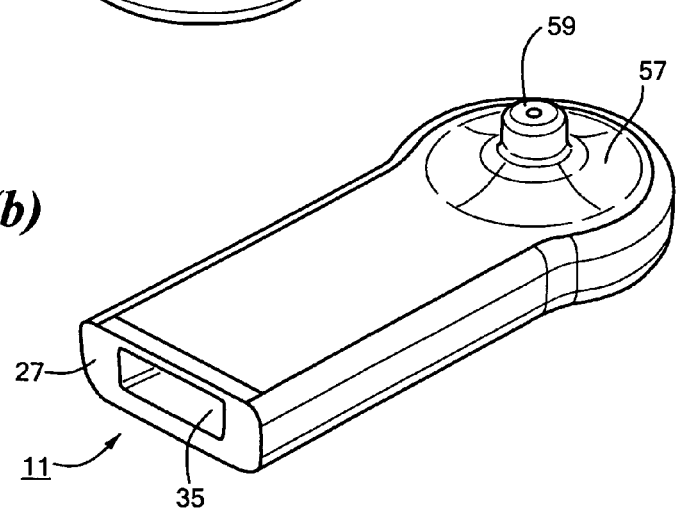
FIG. 1(b) is a top, rear perspective view of the device shown in FIG. 1(a)
Figure 1C:
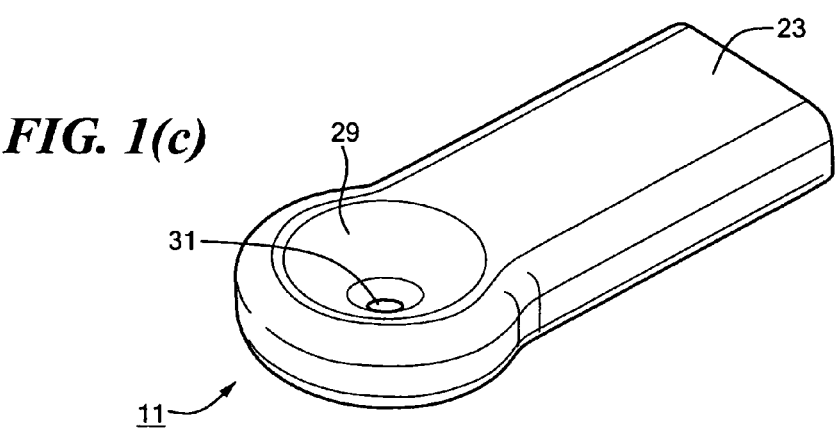
FIG. 1(c) is a bottom, rear perspective view of the device shown in FIG. 1(a)

Referring now to the drawings, there is shown in FIGS. 1(a)-(c) a first embodiment of an analyte test device which is constructed according to the teachings of the present invention, the device being identified generally by reference numeral 11. As will be described further in detail below, device 11 is constructed as a unitary, single-use, disposable cartridge which is adapted to be releasably installed into a compatible analyte test monitor (also referred to herein as an analyte test meter). In conjunction with said analyte test monitor, device 11 is capable of performing both (1) a lancing operation on the skin of a patient in order to draw a sample of blood and (2) an analysis of the concentration of a particular analyte in said blood sample. Because device 11 can be used in conjunction with an analyte test monitor to perform both lancing and analyte concentration measurements, device 11 is also referred to herein as an integrated lancing and analytical device (or simply as an integrated disposable).

Figure 2:
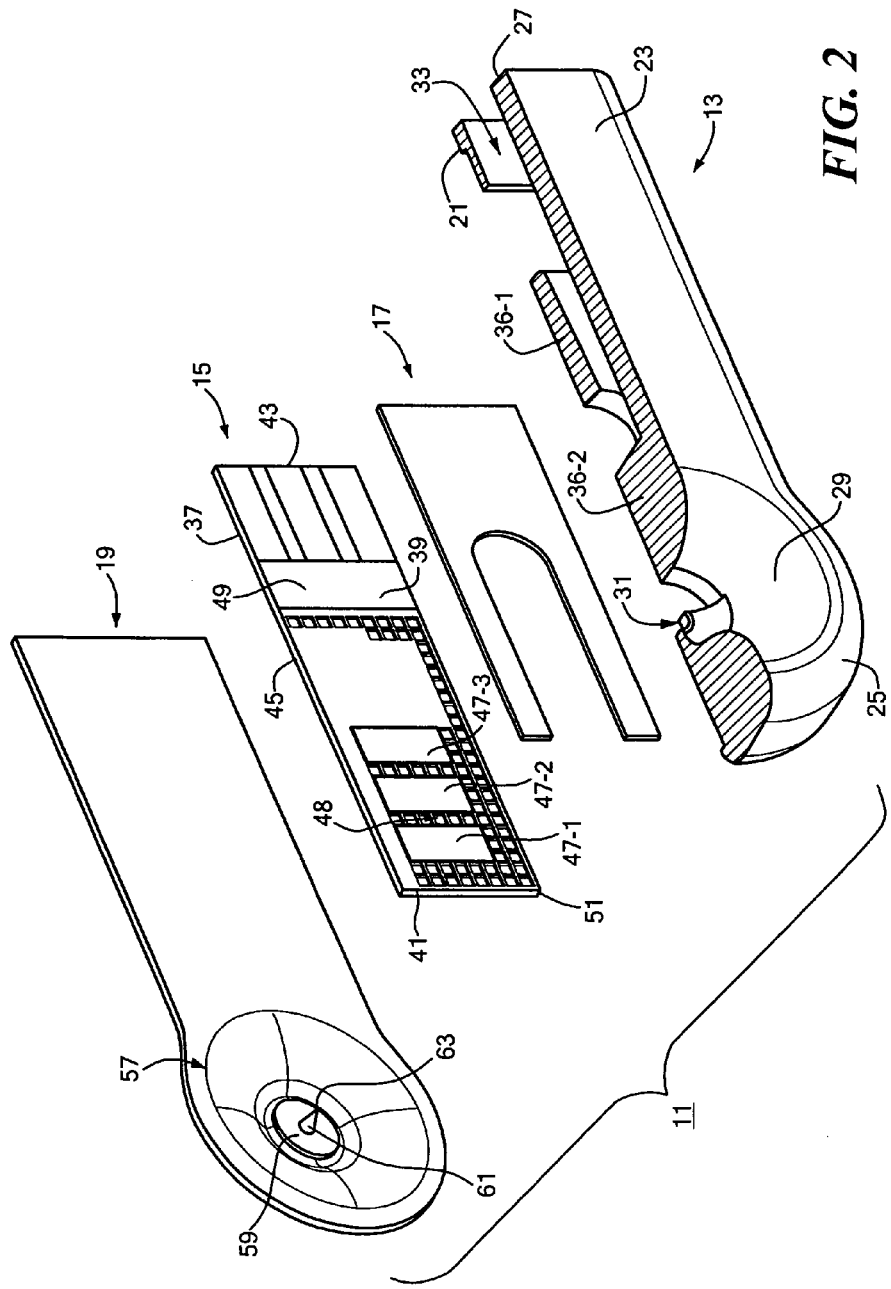
FIG. 2 is an exploded, bottom perspective view of the device shown in FIG. 1(a), the base being shown in section for clarity.

As seen most clearly in FIG. 2, device 11 comprises a base 13, an analyte test strip 15 affixed to base 13 by an adhesive 17, and a cover 19 secured to base 13 over strip 15 to create a unitary, disposable cartridge which preferably has a length of approximately 27 mm, a width of approximately 10 mm and a height of approximately 5 mm. Preferably, device 11 can be mass produced with each individual device 11 enclosed within a hermetically-sealed package to protect against contamination and inadvertent lancing.

Figure 3:
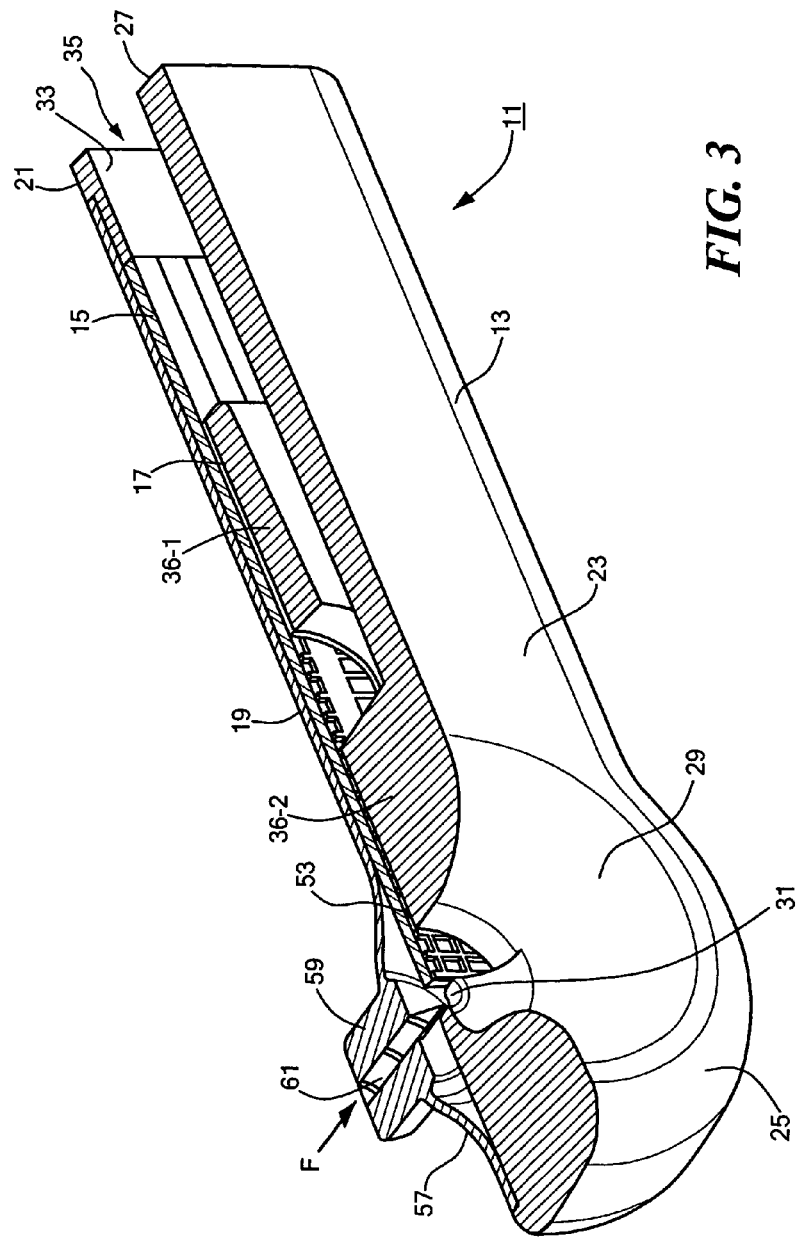
FIG. 3 is a section view of the device shown in FIG. 1(a) taken along lines 3-3.

Referring now to FIGS. 2 and 3, base 13 is a unitary member which is preferably constructed of a rigid and durable plastic material using conventional molding techniques. Base 13 includes a substantially flat top surface 21, a substantially flat bottom surface 23, a rounded first end 25 and a substantially flat second end 27.

Base 13 is shaped to include a skin receiving surface 29 on bottom surface 23 proximate first end 25. Skin receiving surface 29 is represented herein as having a steep inward contour which is substantially rounded. However, it is to be understood that surface 29 is not limited to having a rounded contour. Rather, surface 29 could have an alternative contour (e.g., a squared-off, or stepped, contour with multiple flat surfaces) without departing from the spirit of the present invention.

It should be noted that the surface 29 is adapted to receive the skin of a patient at any one of a variety of different test sites (e.g., the finger of a patient, the forearm of a patient, the thigh of a patient, etc.). In this manner, the patient is able to select a particular site on his/her body which is less sensitive to pain.

As can be appreciated, skin receiving surface 29 has a steep inward contour to maximize the distention (stretching) of the patient's skin pressed thereagainst. In this manner, surface 29 serves to maximize blood flow from the wound site after the lancing procedure, which is highly desirable. Surface 29 is also shaped to define a small, central aperture 31 which extends transversely through top surface 21 and bottom surface 23. As will be described further below, aperture 31 serves as a passageway through which a mechanically-fired lancet travels during the lancing process, which will be described further in detail below.

Although not shown herein, it should be noted that a gasket may be affixed to bottom surface 23 of base 13 immediately surrounding finger receiving surface 29 to create an effective seal between the patient's finger and device 11 without departing from the spirit of the present invention.

As seen most clearly in FIGS. 1(b), 2 and 3, base 13 is additionally shaped to define an interior cavity 33 along a portion of its length, interior cavity 33 being spaced apart and isolated from central aperture 31. Cavity 33 is generally U-shaped in longitudinal cross-section and is externally accessible through a substantially rectangular opening 35 which is formed in second end 27. It should be noted that second end 27 of base 13 is preferably sized and shaped to be in the form of a connector which can matingly engage with a compatible analyte test monitor. Furthermore, with device 11 coupled to said monitor, a connector for a vacuum pump (not shown) contained within said monitor preferably projects through opening 35 and into interior cavity 33.

Base 13 includes a pair of spaced apart platforms 36-1 and 36-2 which partially define interior cavity 33. It should be noted that the top surface of platform 36-2 is disposed slightly beneath the top surface of platform 36-1. Furthermore, it should be noted that the top surface of both platforms 36 is disposed slightly beneath top surface 21 for reasons to become apparent below.

Analyte test strip 15 is preferably in the form of an electrochemical test strip which is constructed to measure the concentration of a particular analyte, such as glucose, in a blood sample applied thereto. Test strip 15 is preferably constructed as a thin, rectangular member which includes a top surface 37, a bottom surface 39, a first end 41 and a second end 43.

Test strip 15 preferably includes a non-conductive substrate 45 and at least a pair of carbon-layer electrodes 47-1 and 47-2 which are deposited onto substrate 37 along a portion of its length in a spaced-apart relationship, electrode 47-1 serving as the reference electrode for test strip 15 and electrode 47-2 serving as the working electrode for test strip 15. An optional third electrode 47-3 may be provided which serves as the trigger electrode for test strip 15 (i.e., an electrode which measures whether an adequate blood sample has been deposited on test strip 15). Together, electrodes 47 define a reaction area 48 proximate first end 41. An enzyme (not shown) which produces an electrical reaction when exposed to a particular analyte (e.g., glucose) is applied to working electrode 47-2 in reaction area 48. In use, a blood sample is deposited across electrodes 47 in reaction area 48 and a voltage provided by the compatible analyte test monitor is applied across electrodes 47 at second end 43, thereby effectively creating a closed circuit. The application of the blood sample on the enzyme deposited on working electrode 47-2 creates an electrical reaction. In response to said reaction, a current (commonly referred to in the art as the working current) is produced which travels along working electrode 47-2, the value of said working current being directly related to the concentration of the particular analyte in the blood sample. Accordingly, with device 11 properly loaded into the compatible analyte test meter, the meter is capable of measuring the value of the working current along working electrode 47-2 and, in turn, using said value to calculate the analyte concentration in the blood sample (e.g., by multiplying said value by a scaling factor).

Test strip 15 may additionally include a non-conductive cover 49 and a mesh fabric 51 which are mounted onto substrate 37 over a portion of electrodes 47, mesh fabric 51 serving to facilitate adequate spreading of a blood sample across reaction area 48. However, it is to be understood that test strip 15 could be provided with an alternative means (other than mesh fabric 51) for spreading (i.e., wicking) a blood sample without departing from the spirit of the present invention.

It should be noted that the present invention is not limited to the particular construction of test strip 15. Rather, it is to be understood that test strip 15 could be replaced with alternative types of conventional analyte test strips without departing from the spirit of the present invention.

Test strip 15 is affixed to base 13 using an adhesive 17. Specifically, bottom surface 39 of test strip 15 is affixed to platform 36-1 in a horizontal orientation by adhesive 17 such that top surface 37 of test strip 15 is substantially flush with top surface 21 of base 13. With test strip 15 affixed to base 13 in this manner, the longitudinal axis of test strip 15 extends substantially parallel to top and bottom surfaces 21 and 23 of base 13.

It should be noted that, since the top surface of platform 36-2 is disposed slightly beneath the top surface of platform 36-1, affixing test strip 15 to platform 36-1 in a horizontal configuration causes first end 41 of test strip 15 to become spaced slightly away from the top surface of platform 36-2. As a consequence, a narrow vacuum path 53 is defined between first end 41 of strip 15 and the top surface of platform 36-2. It should be noted that vacuum path 53 draws aperture 31 in fluid communication with interior cavity 33. Accordingly, the activation of a vacuum pump which includes a connector inserted through opening 35 causes blood expressed from the patient's finger to be drawn into vacuum path 53 from aperture 31 and, in turn, preferably collect entirely within mesh fabric 51 of test strip 15. As can be appreciated, the utilization of vacuum forces to transfer a blood sample from the wound site to the reaction area of test strip 15 minimizes the size of the blood sample which is required to perform an analyte concentration calculation, which is highly desirable and accordingly is a principal feature of the present invention.

It should be noted that test strip 15 is disposed on base 13 such that reaction area 48 of test strip 15 extends at least partially within aperture 31. As a result, reaction area 48 of test strip 15 is disposed in close proximity to the wound site upon lancing, thereby minimizing the distance which the blood sample is required to travel for analysis, which is highly desirable.

It should also be noted that test strip 15 is mounted on base 13 such that electrodes 47 at second end 43 are exposed within interior cavity 33. In this manner, with test strip 15 properly installed into a compatible monitor, a conductive element (e.g., a metal clip) from the monitor can project through opening 35, enter into interior cavity 33 and directly contact electrodes 47, thereby establishing an electrical path between test strip 15 and the monitor. As such, working current present on working electrode 47-2 can be readily measured by the monitor, which is highly desirable.

It should further be noted that test strip 15 may be constructed to include calibration information directly thereon, said calibration information being stored in any conventional medium (e.g., as a barcode, read-only memory (ROM), one or more resistors, a particular pattern of interconnected conductive pads or a colored window) which can be easily read by the monitor when test strip 15 is properly loaded.

As noted briefly above, cover 19 is secured to top surface 21 of base 13 over test strip 15 to create a unitary, disposable cartridge with lancing and analyte measurement capabilities. Cover 19 is preferably in the form of an elongated, thin, unitary plastic member which is affixed to base 13 using any conventional means of securement (e.g., by means of ultrasonic welding or an adhesive).

Cover 19 is provided with a flexible member 57 at one end, flexible member 57 being represented herein having the shape of a convex dome. Insert molded into the apex of member 57 is a cylindrical plastic plunger 59. In turn, insert molded into plunger 59 is a sharpened lancet 61.

Lancet 61 is represented herein as being in the form of a thin, cylindrically-shaped needle which includes a sharpened tip 63. However, it is to be understood that lancet 61 is not limited to any one particular construction. Rather, it is to be understood that lancet 61 could be of any variety (e.g., an etched and/or multi-tip lancet) without departing from the spirit of the present invention.

Preferably, lancet 61 is orientated with sharpened tip 63 aligned to project through aperture 31 in base 13 but without directly contacting test strip 15. Lancet 61 is additionally positioned such that its longitudinal axis extends substantially orthogonal to top and bottom surfaces 37 and 39 (as well as the longitudinal axis) of test strip 15. As can be appreciated, configuring lancet 61 to extend at a right angle relative to test strip 15 substantially reduces the overall length of device 11 (which is often the most challenging dimension to reduce when attempting to minimize the overall size of an integrated lancing and analytical device).

It should be noted that the application of a downward force F (as represented in FIG. 3) onto the free end of plunger 59 causes member 57 to collapse which, in turn, displaces lancet 61 linearly down through aperture 31 in close proximity, but without actually contacting, first end 41 of analyte test strip 15. With the patient's skin distended against surface 29 on base 13, the linear displacement of lancet 61 ultimately causes sharpened tip 63 to puncture the skin of the patient. Upon the release of force F, the resilient nature of member 57 causes it to return to its original shape which, in turn, pulls lancet 61 back up to its original position.

In use, device 11 can be used in the following manner to acquire a blood sample and, in turn, analyze the concentration of a particular analyte in said blood sample. First, an individual analyte test device 11 is removed from its protective wrapping. Once unpackaged, device 11 is loaded by the patient into the appropriate test port of a compatible analyte test monitor. With device 11 properly installed into the monitor in the manner described above, a vacuum pump connector which is located within the monitor projects through opening 35 in device 11 and into interior cavity 33. In addition, conductive leads in the monitor project through opening 35 and are disposed in electrical contact against electrodes 47-1 and 47-2, thereby establishing a current path between test strip 15 of device 11 and the central processing unit (CPU) of the monitor.

In order to perform an blood test, the patient is required to dispose the desired test site against surface 29. As can be appreciated, the steep inward contour of surface 29 serves to adequately distend the patient's skin, thereby causing the patient's imminent wound site to be replete with blood. With the patient's skin disposed against surface 29, the monitor activates the vacuum pump. As can be appreciated, the activation of the vacuum pump causes the skin of the patient at the test site to further distend, thereby drawing additional blood to the test site surface. However, it is to be understood that activation of the vacuum pump could occur after (rather than prior to) the lancet firing process without departing from the spirit of the present invention.

With the patient's skin disposed against surface 29, the lancet firing mechanism in the monitor is activated (e.g., through the depression of a button). Activation of the firing mechanism causes a hammer or other similar device present in the monitor to apply a considerable downward force F onto the outer surface of plunger 59 which, in turn, drives sharpened tip 63 of lancet 61 through aperture 31 and into the patient's skin. Immediately thereafter, the downward force F onto plunger 59 is removed which causes flexible member 57 to retract lancet 61 to its original position.

Upon lancing the patient's skin, the vacuum pump draws blood from the wound site up to vacuum path 53 and directly into mesh fabric 51 of test strip 15. Because mesh fabric 51 extends into vacuum path 53, the application of a vacuum causes the blood sample to be effectively transferred onto mesh fabric 51, thereby minimizing the size of the blood sample which is required for analysis. Preferably, mesh fabric 51 is optimized to absorb the entire blood sample which is drawn into vacuum path 53. In this manner, mesh fabric 51 serves as an effective barrier for preventing blood drawn from the wound site to enter into interior cavity 33 and, in turn, into the monitor. Rather, the particular design of device 11 retains the entire blood sample within the integrated disposable cartridge 11, thereby keeping the analyte test monitor free from contamination by the blood sample, which is highly desirable.

Once an adequate blood sample is applied onto the reaction area of test strip 15, trigger electrode 47-3 sends an appropriate signal to the CPU of the monitor which, in turn, terminates operation of the vacuum pump. The monitor then measures the working current present along working electrode 47-2 (the working current resulting from the reaction between the enzyme present on electrode 47-2 and the blood sample applied thereto). Once the monitor measures the working current, the CPU calculates the concentration of the analyte in the blood sample using the working current (e.g., by multiplying the working current by a known scaling factor). The results of said calculation are preferably shown on a digital display on the monitor.

Upon completion of the assay, the individual device 11 is removed from the monitor and, in a subsequent step, is discarded. In this manner, it is to be understood that device 11 is designed as a single-use, disposable cartridge. Any additional testing can be performed in the same manner as described above using additional cartridges 11.

It should be noted that numerous modifications could be made to device 11 without departing from the spirit of the present invention. For example, it is to be understood that device 11 could be modified to accommodate alternative lancing mechanisms, as will be described further in detail below.

Figure 4A:
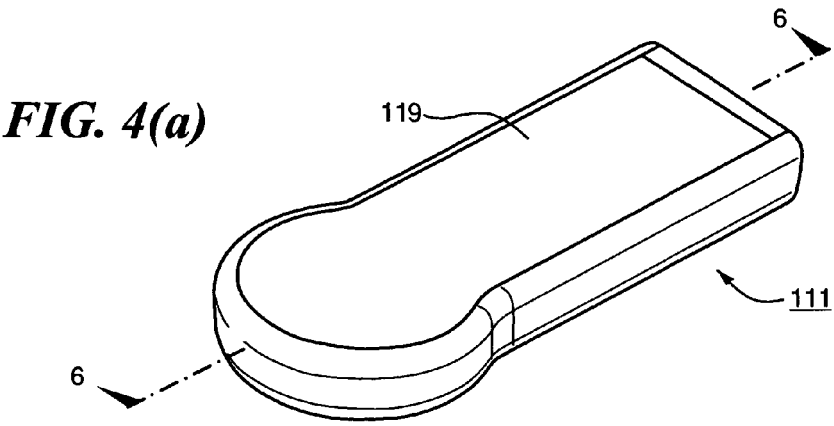
FIG. 4(a) is a top, front perspective view of a second embodiment of an analyte test device which is constructed according to the teachings of the present invention.
Figure 4B:
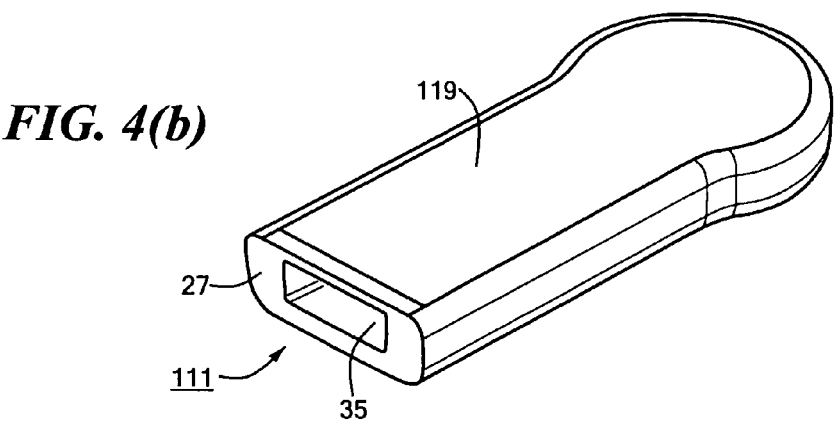
FIG. 4(b) is a top, rear perspective view of the device shown in FIG. 4(a)
Figure 4C:
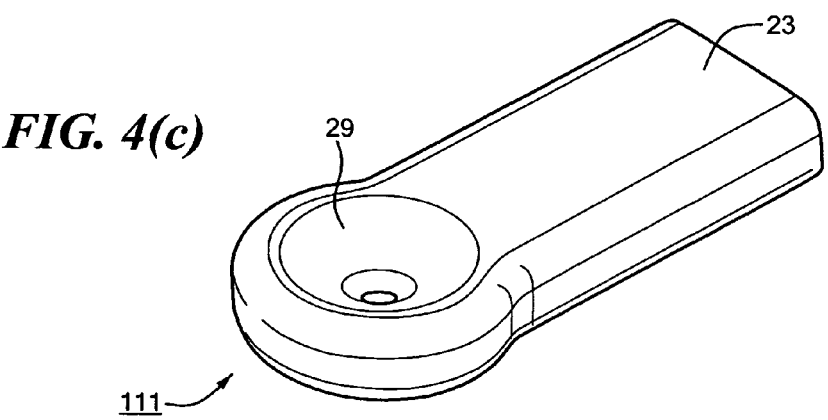
FIG. 4(c) is a bottom, rear perspective view of the device shown in FIG. 4(a)

Specifically, referring now to FIGS. 4(*a*)-(*c*), there is shown a second embodiment of an analyte test device which is constructed according to the teachings of the present invention, the device being identified generally by reference numeral 111.

Figure 5:
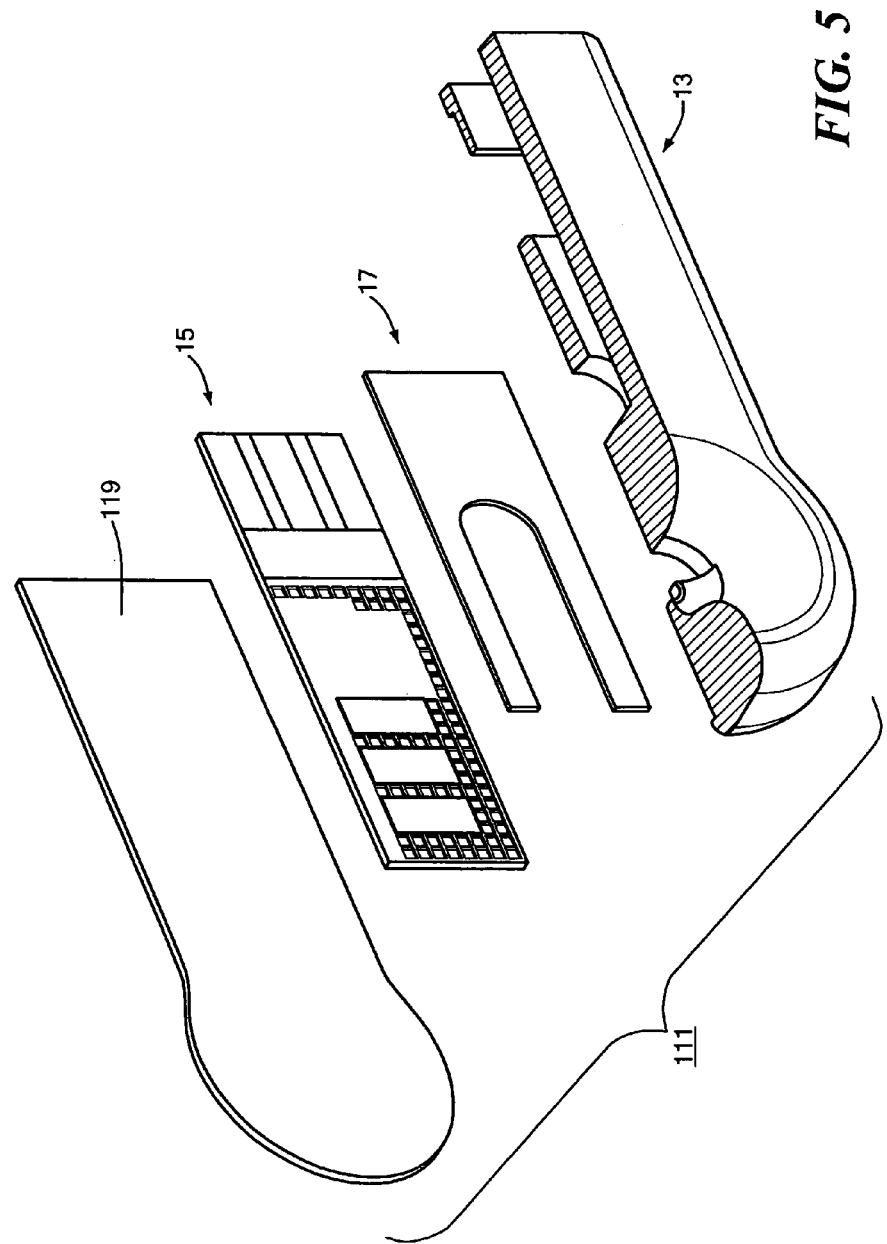
FIG. 5 is an exploded, bottom perspective view of the device shown in FIG. 4(a), the base being shown in section for clarity.
Figure 6:
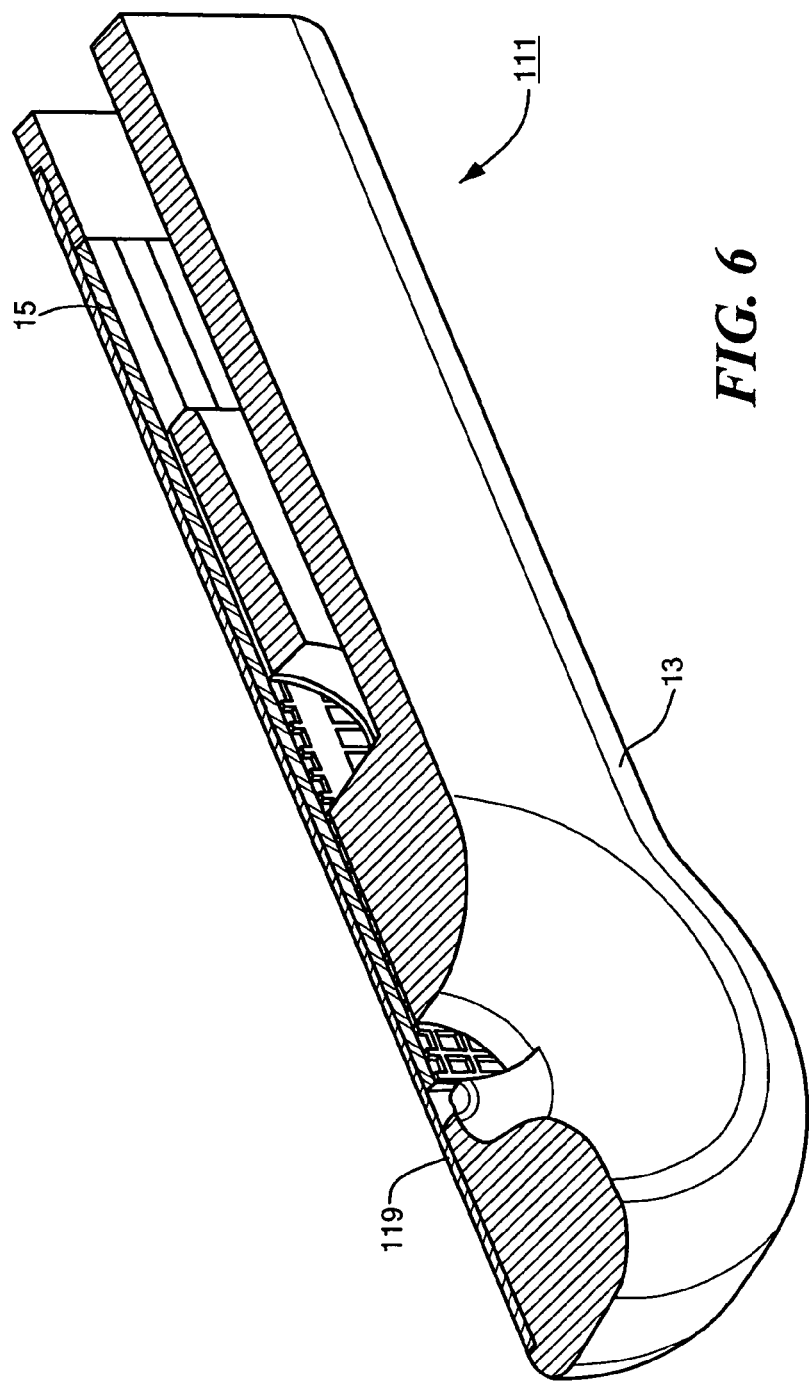
FIG. 6 is a section view of the device shown in FIG. 4(a) taken along lines 6-6.

As seen most clearly in FIGS. 5 and 6, device 111 is similar to device 11 in that device 111 is constructed as a unitary, single-use, disposable cartridge which includes a base 13 and an analyte test strip 15 affixed to base 13 by an adhesive 17.

Device 111 differs from device 11 in that device 111 comprises a cover 119 which differs in construction from cover 19 in device 11. Specifically, cover 119 is constructed as a thin, transparent sheet of plastic material which is secured to base 13 over test strip 15 to create a unitary, single-use, disposable cartridge with lancing and analyte measurement capabilities. Cover 119 is preferably affixed to base 13 using any conventional means of securement (e.g., by means of ultrasonic welding, an adhesive or heat stakes).

It should be noted that device 111 is designed for use in conjunction with an analyte test monitor which includes a laser for lancing. In this manner, cover 119 functions as a transparent window through which a laser beam can pass and ultimately lance the skin of a patient.

Referring now to FIGS. 7(a)-(d), there is shown a third embodiment of an analyte test device which is constructed according to the teachings of the present invention, the device being identified generally by reference numeral 211. Device 211 is similar to device 11 in that device 211 is constructed as a unitary, single-use, disposable cartridge which is adapted to be releasably installed into a compatible analyte test monitor. In conjunction with said analyte test monitor, device 211 is capable of performing both (1) a lancing operation on the skin of a patient in order to draw a sample of blood and (2) an analysis of the concentration of a particular analyte in said blood sample. Because device 211 can be used in conjunction with an analyte test monitor to perform both lancing and analyte concentration measurements, device 211 is also referred to herein as an integrated lancing and analytical device (or simply as an integrated disposable). Preferably, device 211 can be mass produced with each individual device 211 enclosed within a hermetically-sealed package to protect against contamination and inadvertent lancing.

Device 211 comprises an analyte test strip 213, a ring-shaped pad 215 of sticky material affixed to the underside of test strip 213, an outer protective layer 217 affixed to the underside of test strip 213 over pad 215 and a flexible member 219 affixed to the topside of test strip 213.

Analyte test strip 213 is preferably in the form of an electrochemical test strip which is constructed to measure the concentration of a particular analyte, such as glucose, in a blood sample applied thereto.

Test strip 213 preferably includes a non-conductive substrate 221 which is formed as a thin, rectangular strip. Substrate 221 is shaped to include a substantially flat top surface 223, a substantially flat bottom surface 225, a first end 227 and a second end 229. Substrate 221 is additionally shaped to include a small circular aperture 231 proximate first end 227 which extends transversely through top surface 223 and bottom surface 225.

At least a pair of carbon-layer electrodes 233-1 and 233-2 are deposited onto top surface 223 of substrate 221 along a portion of its length in a spaced-apart relationship, electrode 233-1 serving as the reference electrode for test strip 213 and electrode 233-2 serving as the working electrode for test strip 213. An optional third electrode 233-3 may be provided which serves as the trigger electrode for test strip 213 (i.e., an electrode which measures whether an adequate blood sample has been deposited on test strip 213). Together, electrodes 233 define a reaction area 234 proximate aperture 231. An enzyme (not shown) which produces an electrical reaction when exposed to a particular analyte (e.g., glucose) is applied to working electrode 233-2 within reaction area 234.

In use, a blood sample is deposited across electrodes 233 at first end 227 and a voltage provided by the compatible analyte test monitor is applied across electrodes 233-1 and 233-2 at second end 229, thereby effectively creating a closed circuit. The application of the blood sample on the enzyme deposited on working electrode 233-2 creates an electrical reaction. In response to said reaction, a current (commonly referred to in the art as the working current) is produced which travels along working electrode 233-2, the value of said working current being directly related to the concentration of the particular analyte in the blood sample. Accordingly, with device 211 properly loaded into the compatible analyte test meter, the meter is capable of measuring the value of the working current along working electrode 233-2 and, in turn, using said value to calculate the analyte concentration in the blood sample (e.g., by multiplying said value by a scaling factor).

It should be noted that reaction area 234 is located in close proximity to aperture 231. As a result, reaction area 234 of test strip 213 is disposed in close proximity to the wound site upon lancing, thereby minimizing the distance which the blood sample is required to travel for analysis, which is highly desirable.

Figure 7A:
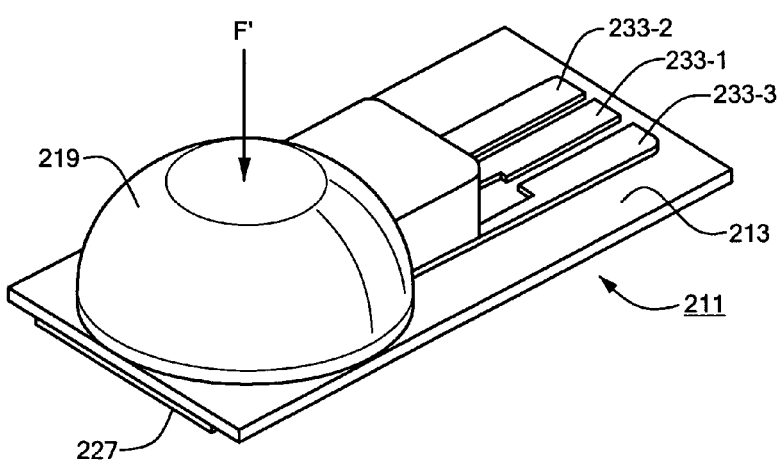
FIG. 7(a) is a top perspective view of a third embodiment of an analyte test device which is constructed according to the teachings of the present invention.
Figure 7B:
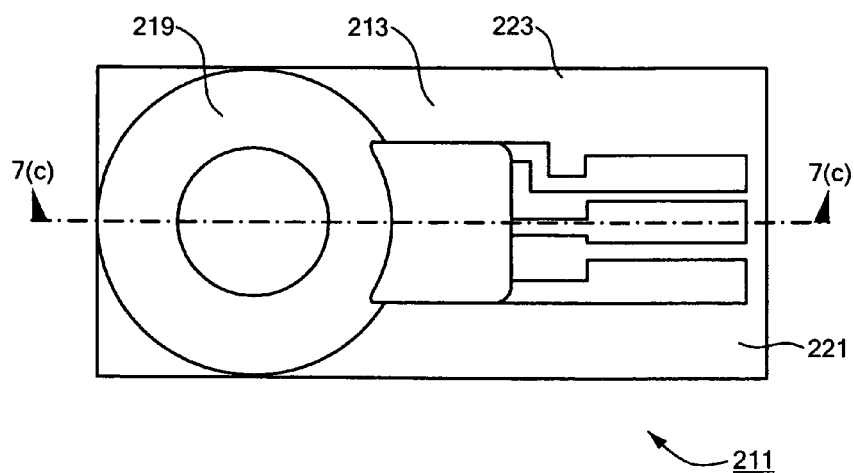
FIG. 7(b) is a top plan view of the device shown in FIG. 7(a)
Figure 7C:
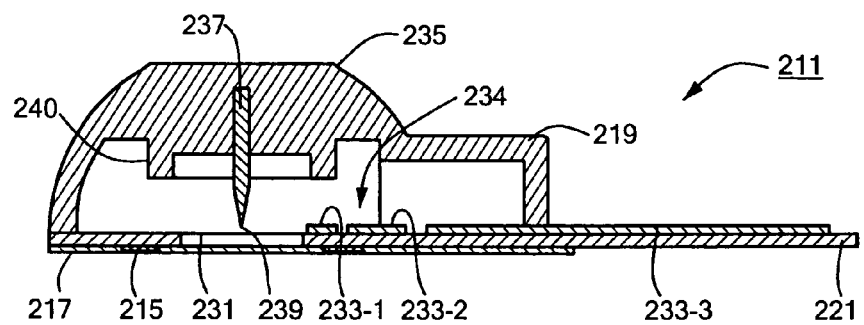
FIG. 7(c) is a section view of the device shown in FIG. 7(a) taken along lines 7(c)-7(c)
Figure 7D:
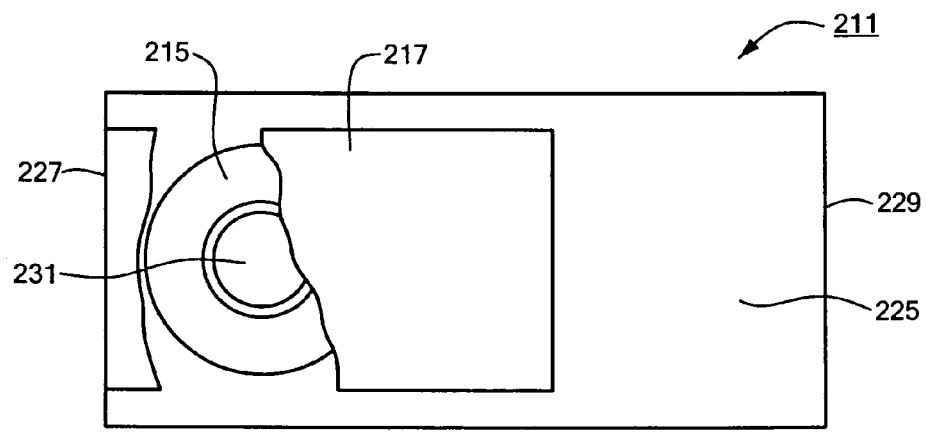
FIG. 7(d) is a bottom plan view of the device shown in FIG. 7(a), the outer protective layer being shown broken away in part.

As seen most clearly in FIG. 7(d), ring-shaped pad 215 is affixed to bottom surface 225 immediately surrounding aperture 231 and is sized and shaped to receive the portion of the patient's skin that is to be lanced. It should be noted that pad 215 is preferably constructed of a sticky material (e.g., an adhesive) which grabs onto the skin of the patient when pressed thereagainst. In this capacity, pad 215 serves to create an effective seal between the skin of the patient and the underside of substrate 221 that immediately surrounds aperture 231.

Outer protective layer 217 is affixed to bottom surface 225 of substrate 221 over pad 215. Layer 217 is constructed as a thin strip of sealing tape having the same approximate length and width as substrate 221. Preferably, the sticky (or tacky) nature of pad 215 serves to secure outer protective layer 217 to substrate 221. With layer 217 affixed to substrate 221, layer 217 serves to enclose aperture 231 and, at the same time, preserve the stickiness of pad 215. When the patient is prepared to use device 211, layer 217 can be peeled off, thereby exposing pad 215 and opening aperture 231.

Figure 8:
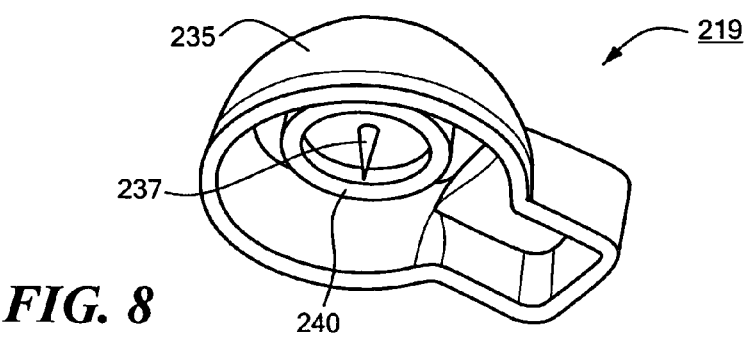
FIG. 8 is a bottom perspective view of the flexible member shown in FIG. 7(a)

Referring now to FIGS. 7(a), 7(c) and 8, flexible member 219 is affixed to top surface 223 of analyte test strip 213 over aperture 231 and reaction area 234 to create a unitary, disposable cartridge with lancing and analyte measurement capabilities. Preferably, flexible member 219 is constructed of a resilient material (e.g., rubber or plastic) which can be secured to test strip 213 by any conventional means (e.g., an adhesive or ultrasonic welding).

Flexible member 219 is shaped to include a convex dome 235. Insert molded into the apex of dome 235 is a sharpened lancet 237. Lancet 237 is represented herein as being in the form of a thin, cylindrically-shaped needle which includes a sharpened tip 239. Preferably, lancet 237 is orientated with sharpened tip 239 aligned to project through aperture 231 in test strip 213. Lancet 237 is molded into dome 235 such that its longitudinal axis extends substantially orthogonal to top and bottom surfaces 223 and 235 (as well as the longitudinal axis) of test strip 213. As can be appreciated, configuring lancet 237 to extend at a right angle relative to test strip 213 substantially reduces the overall length of device 211 (which is often the most challenging dimension to reduce when attempting to minimize the overall size of an integrated lancing and analytical device).

It should be noted that the application of a downward force F' (as represented in FIG. 7(a)) onto the outer surface of dome 235 causes dome 235 to collapse which, in turn, displaces lancet 237 linearly down through aperture 231. With the patient's skin adhered against pad 215, the linear displacement of lancet 237 ultimately causes sharpened tip 239 to puncture the skin of the patient. An annular stop 240 may be integrally formed into the inner surface of dome 235 to limit the degree of downward displacement of lancet 237. Upon the release of force F', the resilient nature of dome 235 causes it to return to its original shape which, in turn, pulls lancet 237 back up to its original position.

As dome 235 collapses, the air pressure within dome 235 increases. Some air will escape from a gap created between test strip 213 and the patient's skin. Ultimately, downward force F' will cause annular stop 240 to stamp on test strip 213. Because sticky pad 215 is disposed on the underside of test strip 213, a tight seal is created between test strip 213 and the patient's skin. As a result, once force F' is released, dome 235 returns to its original configuration which, in turn, creates a vacuum force within dome 235. The vacuum force is responsible for drawing, or expressing, blood from the patient's wound site into dome 235. In this manner, blood drawn from the patient's finger is displaced into reaction area 234 of test strip 213, thereby minimizing the amount of blood which is needed for device 211 to operate, which is highly desirable.

In use, device 211 can be used in the following manner to acquire a blood sample and, in turn, analyze the concentration of a particular analyte in said blood sample. First, an individual analyte test device 211 is removed from its protective wrapping. Once unpackaged, the patient is required to peel off the outer protective layer 217, thereby exposing sticky pad 215. The unwrapped device 211 is then loaded by the patient into the appropriate test port of a compatible analyte test monitor. With device 211 properly installed into the monitor in the manner described above, conductive leads in the monitor are disposed in electrical contact against electrodes 233-1 and 233-2, thereby establishing a current path between test strip 213 and the central processing unit (CPU) of the monitor.

In order to perform an blood test, the patient is required to dispose his/her skin against pad 215. As can be appreciated, the sticky nature of pad 215 creates an effective seal between the skin of the patient and analyte test strip 213. With the patient's skin disposed against pad 215, the lancet firing mechanism in the monitor is activated (e.g., through the depression of a button). Activation of the firing mechanism causes a hammer or other similar device present in the monitor to apply a considerable downward force F' onto the outer surface of dome 235 which, in turn, drives sharpened tip 239 of lancet 237 through aperture 231 and into the patient's finger. Annular stop 240 within dome 235 limits the degree in which dome 235 can collapse, thereby limiting the displacement of lancet 237.

Immediately thereafter, the downward force F' onto dome 235 is removed which causes dome 235 to return to its original shape which, in turn, retracts lancet 237 to its original position. As dome 235 returns to its original shape, a vacuum force is created which draws blood from the wound site and into reaction area 234 of test strip 213. It should be noted that, in this manner, device 211 serves to retain the entire blood sample expressed from the patient's skin within the integrated disposable cartridge 211, thereby keeping the analyte test monitor free from contamination by the blood sample, which is highly desirable.

Once an adequate blood sample is applied onto the reaction area of test strip 213, trigger electrode 233-3 sends an appropriate signal to the CPU of the monitor which, in turn, measures the working current present along working electrode 233-2 (the working current resulting from the reaction between the enzyme present on electrode 233-2 and the blood sample applied thereto). Once the monitor measures the working current, the CPU calculates the concentration of the analyte in the blood sample using the working current (e.g., by multiplying the working current by a known scaling factor). The results of said calculation are preferably shown on a digital display on the monitor.

Upon completion of the assay, the individual device 211 is removed from the monitor and, in a subsequent step, is discarded. In this manner, it is to be understood that device 211 is designed as a single-use, disposable cartridge. Any additional testing can be performed in the same manner as described above using additional cartridges 211.

It should be noted that numerous modifications could be made to device 211 without departing from the spirit of the present invention. For example, referring now to FIGS. 9(a)-(d), there is shown a fourth embodiment of an analyte test device which is constructed according to the teachings of the present invention, the device being identified generally by reference numeral 311. Device 311 is similar to devices 11, 111 and 211 in that device 311 is constructed as a unitary, single-use, disposable cartridge which is adapted to be releasably installed into a compatible analyte test monitor. In conjunction with said analyte test monitor, device 311 is capable of performing both (1) a lancing operation on the skin of a patient in order to draw a sample of blood and (2) an analysis of the concentration of a particular analyte in said blood sample. Because device 311 can be used in conjunction with an analyte test monitor to perform both lancing and analyte concentration measurements, device 311 is also referred to herein as an integrated lancing and analytical device (or simply as an integrated disposable). Preferably, device 311 can be mass produced with each individual device 311 enclosed within a hermetically-sealed package to protect against contamination and inadvertent lancing.

Device 311 comprises an analyte test strip 313, a pad 315 of sticky material affixed to the underside of test strip 313, an outer protective layer 317 affixed to the underside of test strip 313 over pad 315 and a flexible member 319 affixed to the topside of test strip 313.

Analyte test strip 313 is preferably in the form of an electrochemical test strip which is constructed to measure the concentration of a particular analyte, such as glucose, in a blood sample applied thereto.

Test strip 313 preferably includes a non-conductive substrate 321 which is formed as a thin, rectangular strip. Substrate 321 is shaped to include a substantially flat top surface 323, a substantially flat bottom surface 325, a first end 327 and a second end 329. Substrate 321 is additionally shaped to include a small circular aperture 331 proximate first end 327.

At least a pair of carbon-layer electrodes 333-1 and 333-2 are deposited onto bottom surface 325 of substrate 321 along a portion of its length in a spaced-apart relationship, electrode 333-1 serving as the reference electrode for test strip 313 and electrode 333-2 serving as the working electrode for test strip 313. An optional third electrode 333-3 may be provided which serves as the trigger electrode for test strip 313 (i.e., an electrode which measures whether an adequate blood sample has been deposited on test strip 313). Together, electrodes 333 define a reaction area 334 proximate aperture 331. An enzyme (not shown) which produces an electrical reaction when exposed to a particular analyte (e.g., glucose) is applied to working electrode 333-2 within reaction area 334.

In use, a blood sample is deposited across electrodes 333 within reaction area 334 and a voltage provided by the compatible analyte test monitor is applied across electrodes 333-1 and 333-2 at second end 329, thereby effectively creating a closed circuit. The application of the blood sample on the enzyme deposited on working electrode 333-2 creates an electrical reaction. In response to said reaction, a current (commonly referred to in the art as the working current) is produced which travels along working electrode 333-2, the value of said working current being directly related to the concentration of the particular analyte in the blood sample. Accordingly, with device 311 properly loaded into the compatible analyte test meter, the meter is capable of measuring the value of the working current along working electrode 333-2 and, in turn, using said value to calculate the analyte concentration in the blood sample (e.g., by multiplying said value by a scaling factor).

It should be noted that the enzyme is deposited on working electrode 333-2 in close proximity to aperture 331. As a result, reaction area 334 of test strip 313 is disposed in close proximity to the wound site upon lancing, thereby minimizing the distance which the blood sample is required to travel for analysis, which is highly desirable.

Figure 9A:
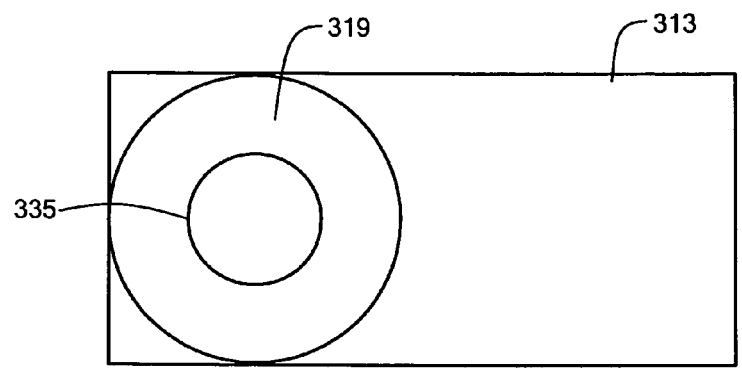
FIG. 9(a) is a top plan view of a fourth embodiment of an analyte test device which is constructed according to the teachings of the present invention.
Figure 9B:
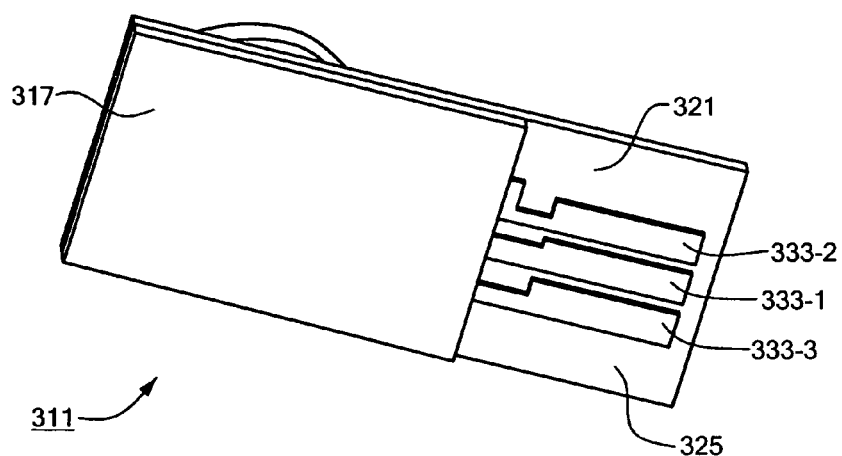
FIG. 9(b) is a bottom perspective view of the device shown in FIG. 9(a)
Figure 9C:
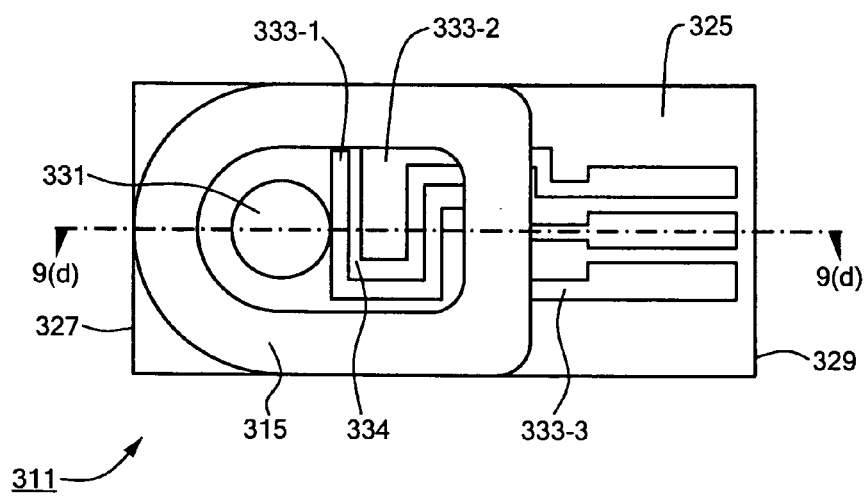
FIG. 9(c) is a bottom plan view of the device shown in FIG. 9(a), the device being shown with the sticky pad removed therefrom.

As seen most clearly in FIG. 9(c), pad 315 is affixed to bottom surface 325 and is sized and shaped to receive a portion of the patient's skin (e.g., a fingertip) that is to be lanced. Pad 315 is shaped so as to circumscribe aperture 331 as well as reaction area 334. It should be noted that pad 315 is preferably constructed of a sticky material (e.g., an adhesive) which grabs onto the skin of the patient's finger when pressed thereagainst. In this capacity, pad 315 serves to create an effective seal between the skin of the patient's finger and the underside of substrate 321 immediately surrounding aperture 231.

Outer protective layer 317 is affixed to bottom surface 325 of substrate 321 over pad 315. Preferably, the sticky (or tacky) nature of pad 315 serves to secure outer protective layer 317 to substrate 321. With layer 317 affixed to pad 315, layer 317 serves to enclose aperture 331, prevent contamination of reaction area 334, and preserve the stickiness of pad 315. When the patient is prepared to use device 311, layer 317 can be peeled off, thereby exposing pad 315 and opening aperture 331.

Figure 9D:
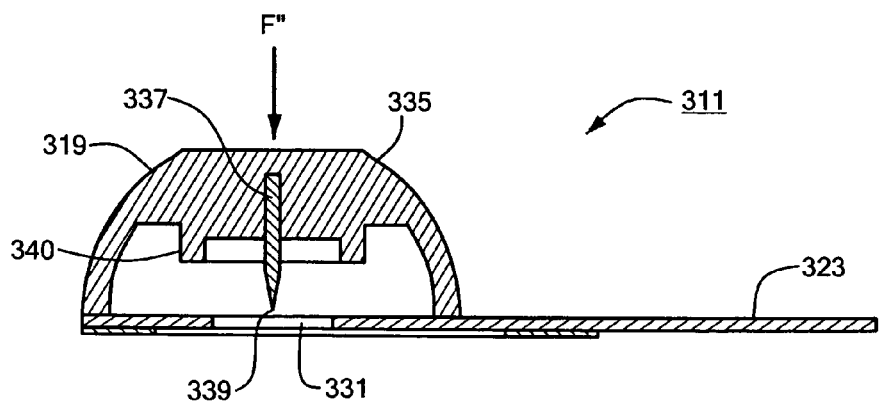
FIG. 9(d) is a section view of the device shown in FIG. 9(c) taken along lines 9(d)-9(d).

Referring now to FIGS. 9(a) and 9(d), flexible member 319 is affixed to top surface 323 of analyte test strip 313 over aperture 331 to create a unitary, disposable cartridge with lancing and analyte measurement capabilities. Preferably, flexible member 319 is constructed of a resilient material (e.g., rubber or plastic) which can be secured to test strip 313 by any conventional means (e.g., an adhesive or ultrasonic welding).

Flexible member 319 is shaped to include a convex dome 335. Insert molded into the apex of dome 335 is a sharpened lancet 337. Lancet 337 is represented herein as being in the form of a thin, cylindrically-shaped needle which includes a sharpened tip 339. Preferably, lancet 337 is orientated with sharpened tip 339 aligned to project through aperture 331 in test strip 313. Lancet 337 is molded into dome 335 such that its longitudinal axis extends substantially orthogonal to top and bottom surfaces 323 and 335 (as well as the longitudinal axis) of test strip 313. As can be appreciated, configuring lancet 337 to extend at a right angle relative to test strip 313 substantially reduces the overall length of device 311 (which is often the most challenging dimension to reduce when attempting to minimize the overall size of an integrated lancing and analytical device).

It should be noted that the application of a downward force F''' (as represented in FIG. 9) onto the outer surface of dome 335 causes dome 335 to collapse which, in turn, displaces lancet 337 linearly down through aperture 331. With the patient's skin stuck against pad 315, the linear displacement of lancet 337 ultimately causes sharpened tip 339 to puncture the skin of the patient. An annular stop 340 may be integrally formed into the inner surface of dome 335 to limit the degree of downward displacement of lancet 337. Upon the release of force F''', the resilient nature of dome 335 causes it to return to its original shape which, in turn, pulls lancet 337 back up to its original position.

As dome 335 collapses, the air pressure within dome 335 increases. Some air will escape from a gap created between test strip 313 and the patient's skin. Ultimately, downward force F''' will cause annular stop 340 to stamp on test strip 313. Because pad 315 is disposed on the underside of test strip 313, a tight seal is created between test strip 313 and the patient's skin. As a result, once force F''' is released, dome 335 returns to its original configuration which, in turn, creates a vacuum force within dome 335. The vacuum force is responsible for drawing, or expressing, blood from the patient's wound site and into reaction area 334, thereby minimizing the amount of blood which is needed for device 311 to operate, which is highly desirable.

The embodiments shown in the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. An analyte test device, comprising:
    a housing shaped to define an aperture for receiving a body fluid sample through the skin of a patient disposed at the aperture, the housing defining a cavity spaced apart and isolated from the aperture, the cavity being externally accessible through an opening;
    an analyte test sensor coupled within said housing such that said test sensor is exposed to both of said aperture and said cavity, said test sensor comprising a reaction area defined between a plurality of electrodes, said test sensor configured such that a vacuum path is formed between said test sensor and a surface within said housing such that said body fluid sample is drawn from said aperture to said reaction area and prevented from entering said cavity during a process for analyte testing of said body fluid sample;
    a mechanically-fired lancet coupled within said housing and disposed for projecting through said aperture for puncturing said skin of said patient,
    wherein said test sensor is adapted to collect said body fluid sample at said reaction area from said patient through said aperture and said vacuum path after said puncturing of said skin of said patient without moving said skin of said patient relative to its position during puncturing, and
    wherein said housing comprises a skin receiving surface around said aperture, and wherein the skin receiving surface has an inward contour which is substantially rounded.

2. The analyte test device as claimed in claim 1, further comprising a gasket, wherein said gasket comprises a ring-shaped pad constructed of a sticky material which is adapted to be pressed against the patient's skin and to grab the skin when so pressed.

3. The analyte test device as claimed in claim 2, further comprising an outer protective layer over said ring-shaped pad which can be peeled off, thereby exposing pad and aperture.

4. An analyte test device, comprising:
- a housing shaped to define an aperture for receiving a body fluid sample through the skin of a patient disposed at the aperture, the housing defining a cavity spaced apart and isolated from the aperture, the cavity being externally accessible through an opening;
- an analyte test sensor coupled within said housing such that said test sensor is exposed to both of said aperture and said cavity, said test sensor comprising a reaction area defined between a plurality of electrodes, said test sensor configured such that a vacuum path is formed between said test sensor and a surface within said housing such that said body fluid sample is drawn from said aperture to said reaction area and prevented from entering said cavity during a process for analyte testing of said body fluid sample;
- a mechanically-fired lancet coupled within said housing and disposed for projecting through said aperture for puncturing said skin of said patient,
- wherein said test sensor is adapted to collect said body fluid sample at said reaction area from said patient through said aperture and said vacuum path after said puncturing of said skin of said patient without moving said skin of said patient relative to its position during puncturing,
- wherein said housing comprises a skin receiving surface around said aperture, and a gasket coupled to said housing immediately surrounding said skin receiving surface to create an effective seal between the patient's skin and the device; and
- wherein the skin receiving surface has an inward contour which is substantially rounded.

5. The analyte test device as claimed in claim 4, wherein said device is constructed as a unitary, single-use, disposable cartridge.

6. The analyte test device as claimed in claim 4, wherein the interior cavity is externally accessible through said opening.

7. The analyte test device as claimed in claim 4, wherein a bottom surface of said housing is shaped to include said skin receiving surface.

8. The analyte test device as claimed in claim 7, wherein the skin receiving surface at least partially defines the aperture in said housing.

9. The analyte test device as claimed in claim 4, wherein said analyte test sensor comprises an electrochemical analyte test sensor which comprises said reaction area.

10. The analyte test device as claimed in claim 9, wherein the reaction area of said test sensor is disposed to project into said vacuum path.

11. The analyte test device as claimed in claim 9, wherein the reaction area of said test sensor is disposed to project into said aperture.

12. The analyte test device as claimed in claim 9, wherein a cover layer of said test sensor is affixed to a base layer of said test sensor using an adhesive.

13. The analyte test device as claimed in claim 9, wherein at least a portion of said electrodes are externally accessible.

14. The analyte test device as claimed in claim 9 wherein said device is constructed as a unitary, single-use, disposable cartridge.

15. The analyte test device as claimed in claim 4, wherein a cover of the device is constructed of a transparent material.

16. The analyte test device as claimed in claim 4, wherein said lancet is orientated such that its longitudinal axis extends at an approximate right angle relative to the longitudinal axis of said analyte test sensor.

17. The analyte test device as claimed in claim 4, wherein said lancet is aligned to project through the aperture in said base upon deformation of a flexible dome-shaped member.

18. The analyte test sensor as claimed in claim 4, wherein said lancet is adapted to selectively penetrate through the aperture in the housing.

19. The analyte test device as claimed in claim 4, further comprising a pad coupled to a bottom surface of the said test sensor.

20. The analyte test device as claimed in claim 19 further comprising a protective layer coupled to the bottom surface of said test sensor over said pad.

21. The analyte test device as claimed in claim 20 wherein said protective layer is constructed as a thin layer of sealing tape.

22. The analyte test device as claimed in claim 19 wherein said lancet is aligned to project through said aperture defined in the bottom surface of the test sensor.

23. The analyte test device as claimed in claim 4 further comprising a flexible member coupled to the lancet.

24. The analyte test device as claimed in claim 23 wherein said lancet is orientated such that its longitudinal axis extends at an approximate right angle relative to the longitudinal axis of said analyte test sensor.

25. The analyte test device as claimed in claim 4, wherein said gasket comprises a ring-shaped pad constructed of a sticky material which is adapted to be pressed against the patient's skin and to grab the skin when so pressed.

26. The analyte test device as claimed in claim 25, further comprising an outer protective layer over said ring-shaped pad which can be peeled off, thereby exposing pad and aperture.

27. The analyte test device as claimed in claim 1 wherein said device is constructed as a unitary, single-use, disposable cartridge.

28. The analyte test device as claimed in claim 1 wherein the interior cavity is externally accessible through said opening.

29. The analyte test device as claimed in claim 1 wherein a bottom surface of said housing is shaped to include said skin receiving surface.

30. The analyte test device as claimed in claim 29 wherein the skin receiving surface at least partially defines the aperture in said housing.

31. The analyte test device as claimed in claim 1 wherein said analyte test sensor comprises an electrochemical analyte test sensor which comprises said reaction area.

32. The analyte test device as claimed in claim 31 wherein the reaction area of said test sensor is disposed to project into said vacuum path.

33. The analyte test device as claimed in claim 31 wherein the reaction area of said test sensor is disposed to project into said aperture.

34. The analyte test device as claimed in claim 31 wherein a cover layer of said test sensor is affixed to a base layer of said test sensor using an adhesive.

35. The analyte test device as claimed in claim 31 wherein at least a portion of said electrodes are externally accessible.

36. The analyte test device as claimed in claim 1 wherein a cover of the device is constructed of a transparent material.

37. The analyte test device as claimed in claim 1 wherein said lancet is orientated such that its longitudinal axis extends at an approximate right angle relative to the longitudinal axis of said analyte test sensor.

38. The analyte test device as claimed in claim 1 wherein said lancet is aligned to project through the aperture in said base upon deformation of a flexible dome-shaped member.

39. The analyte test sensor of claim 1, wherein said lancet is adapted to selectively penetrate through the aperture in the housing.

40. The analyte test device as claimed in claim 31 wherein said device is constructed as a unitary, single-use, disposable cartridge.

41. The analyte test device as claimed in claim 1 further comprising a pad coupled to a bottom surface of the said test sensor.

42. The analyte test device as claimed in claim 41 further comprising a protective layer coupled to the bottom surface of said test sensor over said pad.

43. The analyte test device as claimed in claim 42 wherein said protective layer is constructed as a thin layer of sealing tape.

44. The analyte test device as claimed in claim 1 further comprising a flexible member coupled to the lancet.

45. The analyte test device as claimed in claim 44 wherein said lancet is orientated such that its longitudinal axis extends at an approximate right angle relative to the longitudinal axis of said analyte test sensor.

46. The analyte test device as claimed in claim 41 wherein said lancet is aligned to project through said aperture defined in the bottom surface of the test sensor.

47. The analyte test device as claimed in claim 1, wherein the cavity is U-shaped in longitudinal cross-section.

\* \* \* \* \*